United States Patent [19]
Knowlton et al.

[11] Patent Number: 5,805,281
[45] Date of Patent: Sep. 8, 1998

[54] NOISE REDUCTION UTILIZING SIGNAL MULTIPLICATION

[75] Inventors: Dennis J. Knowlton; Edward R. Green, both of Boulder, Colo.

[73] Assignee: Particle Measuring Systems, Boulder, Colo.

[21] Appl. No.: 845,223

[22] Filed: Apr. 21, 1997

[51] Int. Cl.$^6$ .................................................. G01N 15/14
[52] U.S. Cl. ...................... 356/336; 356/343; 250/208.2; 250/574
[58] Field of Search .................................. 356/336, 343, 356/237; 250/208.2, 574

[56] References Cited

U.S. PATENT DOCUMENTS

| | | | |
|---|---|---|---|
| 4,893,928 | 1/1990 | Knollenberg | 356/336 |
| 4,917,496 | 4/1990 | Sommer | 356/336 |
| 5,090,808 | 2/1992 | Ishikawa et al. | 356/336 |
| 5,153,926 | 10/1992 | Jansson et al. | 382/54 |
| 5,329,351 | 7/1994 | Clementi | 356/237 |
| 5,467,189 | 11/1995 | Kreikebaum et al. | 356/336 |

FOREIGN PATENT DOCUMENTS 4-289440  10/1992  Japan ....................................... 356/336

*Primary Examiner*—Richard A. Rosenberger
*Attorney, Agent, or Firm*—Robert E. Harris

[57] ABSTRACT

Noise reduction is effected by multiplying together electrical signals that include pulses embedded in noise, with the pulses being indicative of the same event, such as light scattered by particles, occurring at a viewing area, and with the signals being processed prior to multiplication so that the pulses and the variance of the noise in the electrical signals are multiplied by one another. A detector in each of a plurality of channels detects the events occurring at the common viewing area and provides pulses indicative thereof, and the output from each detector is amplified, passed through matched low-pass filters to enhance pulse detection, and then passed through a baseline restorer to remove DC components from the noise then present in the signal, prior to coupling of the signals to a multiplier. At the multiplier, peak values of the pulses included in the signals from each of the channels multiply, as do the variances of the uncorrelated noise included in the signals from each of the channels, resulting in multiplication of the signal-to-noise ratio, and hence improvement in signal-to-noise.

20 Claims, 6 Drawing Sheets

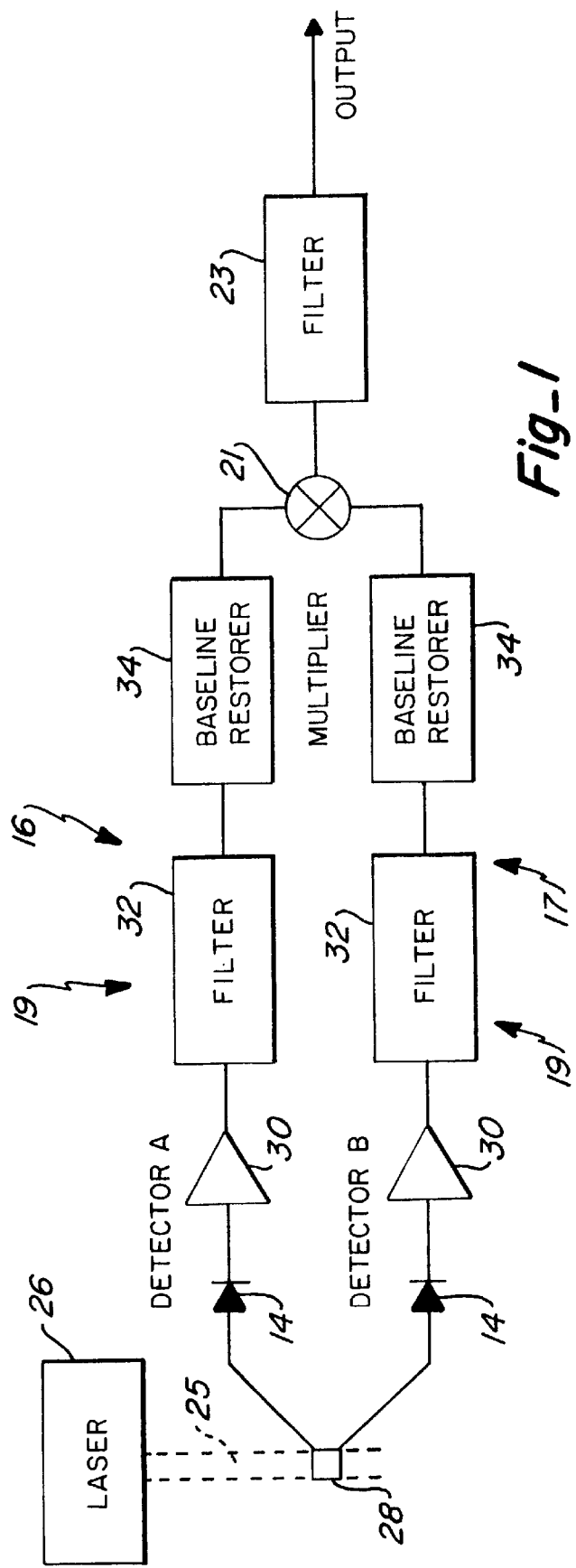
Fig_1
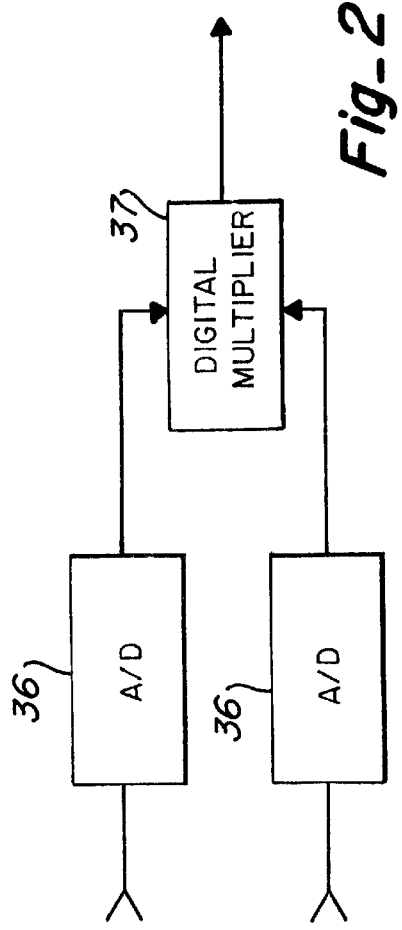
Fig_2

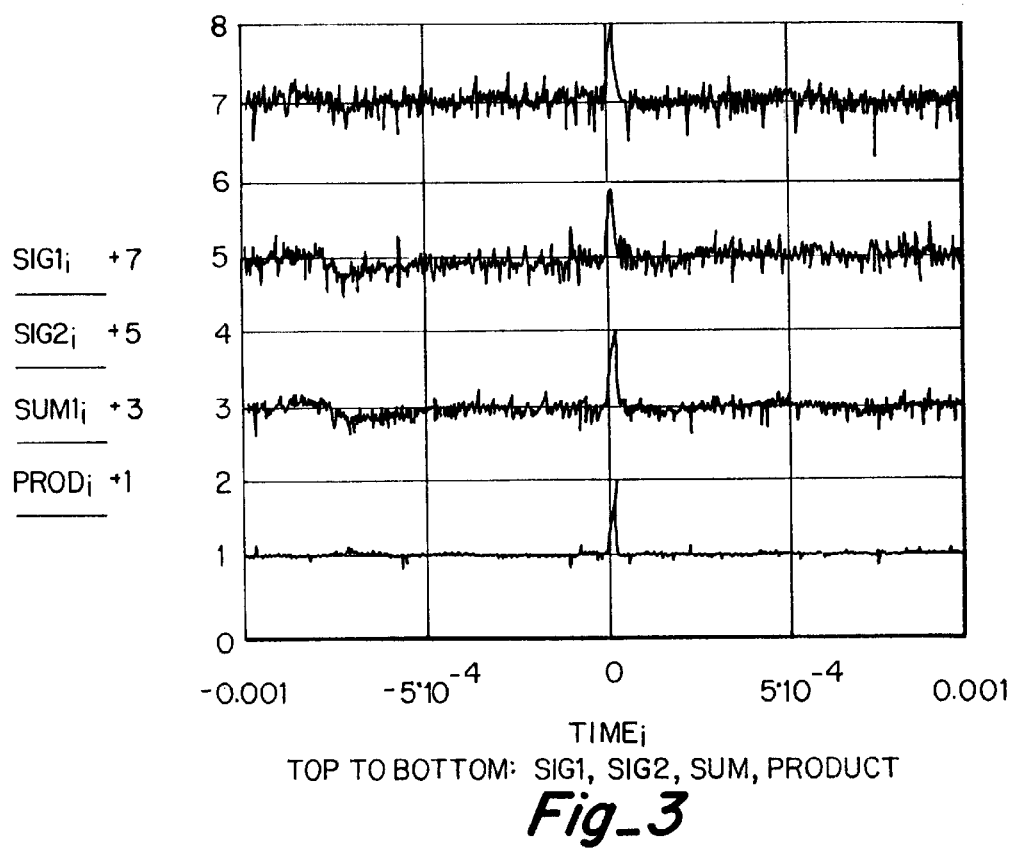
Fig_3
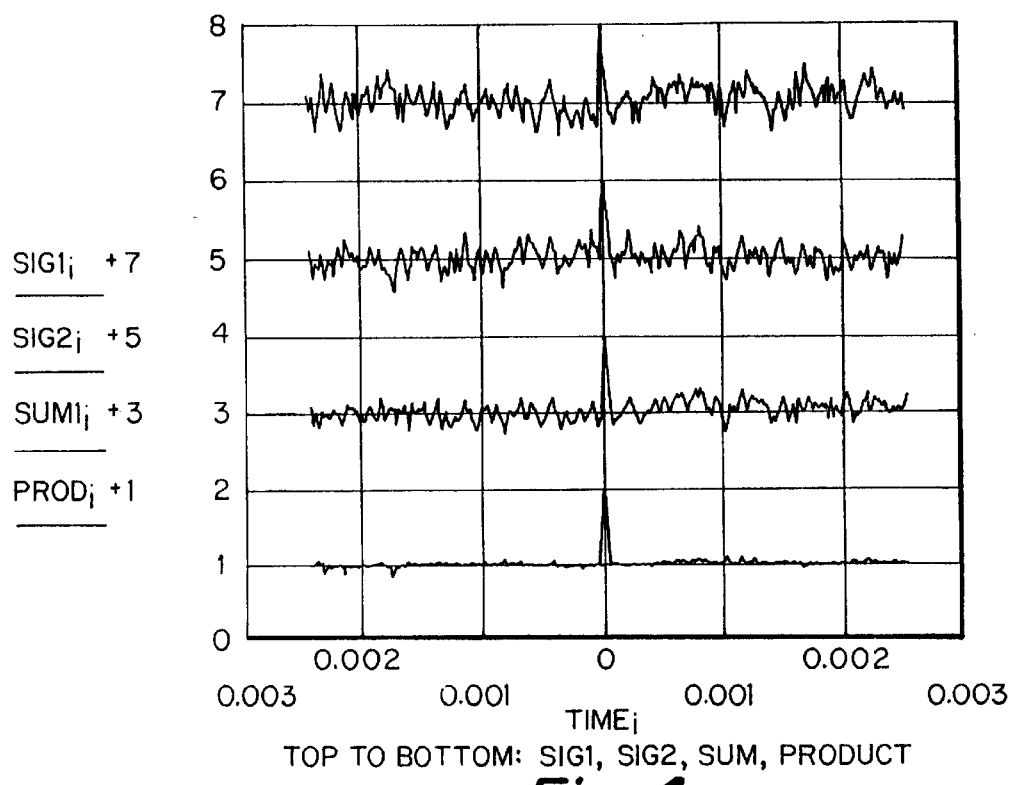
Fig_4

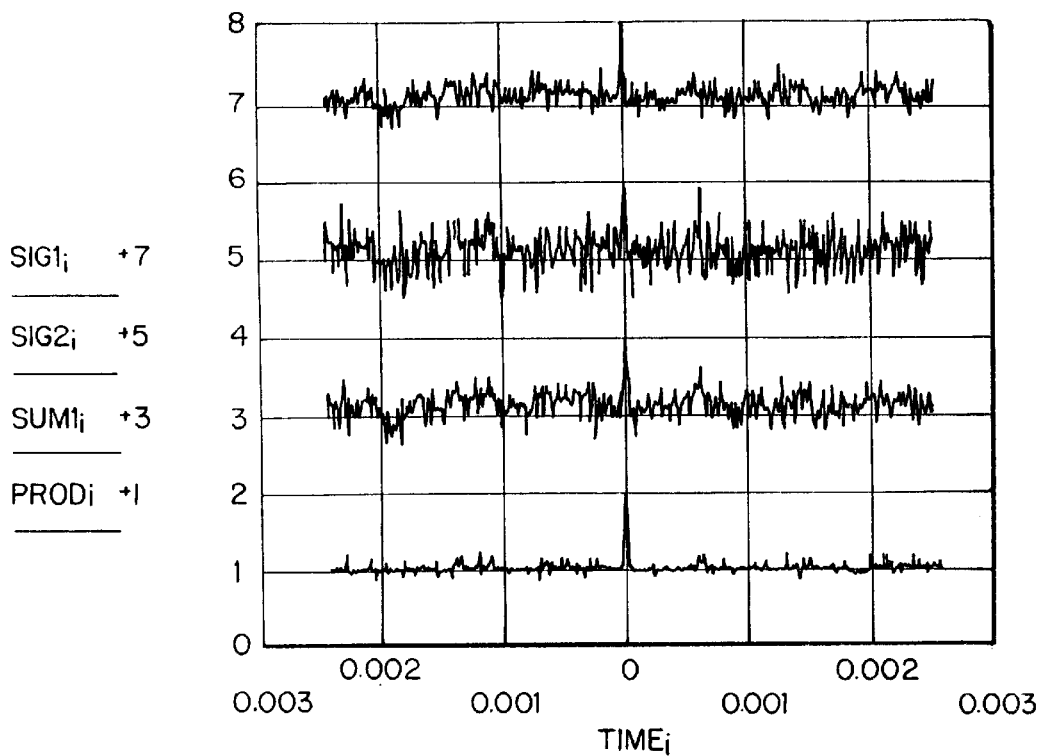
TOP TO BOTTOM: SIG1, SIG2, SUM, PRODUCT
*Fig_5*
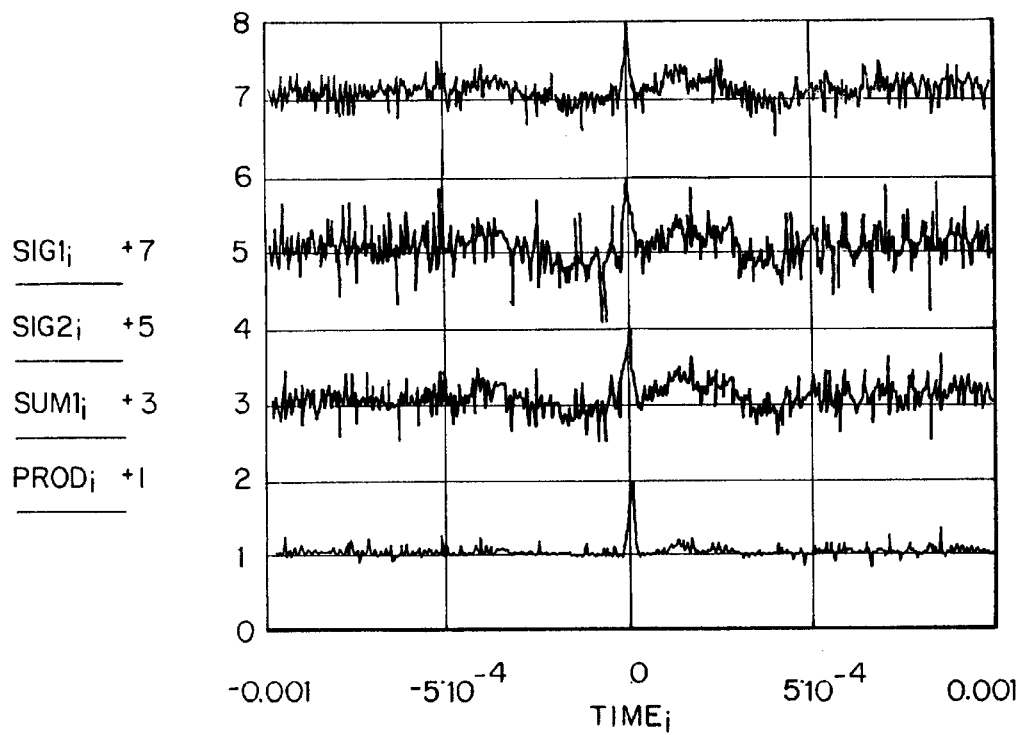
TOP TO BOTTOM: SIG1, SIG2, SUM, PRODUCT
*Fig_6*

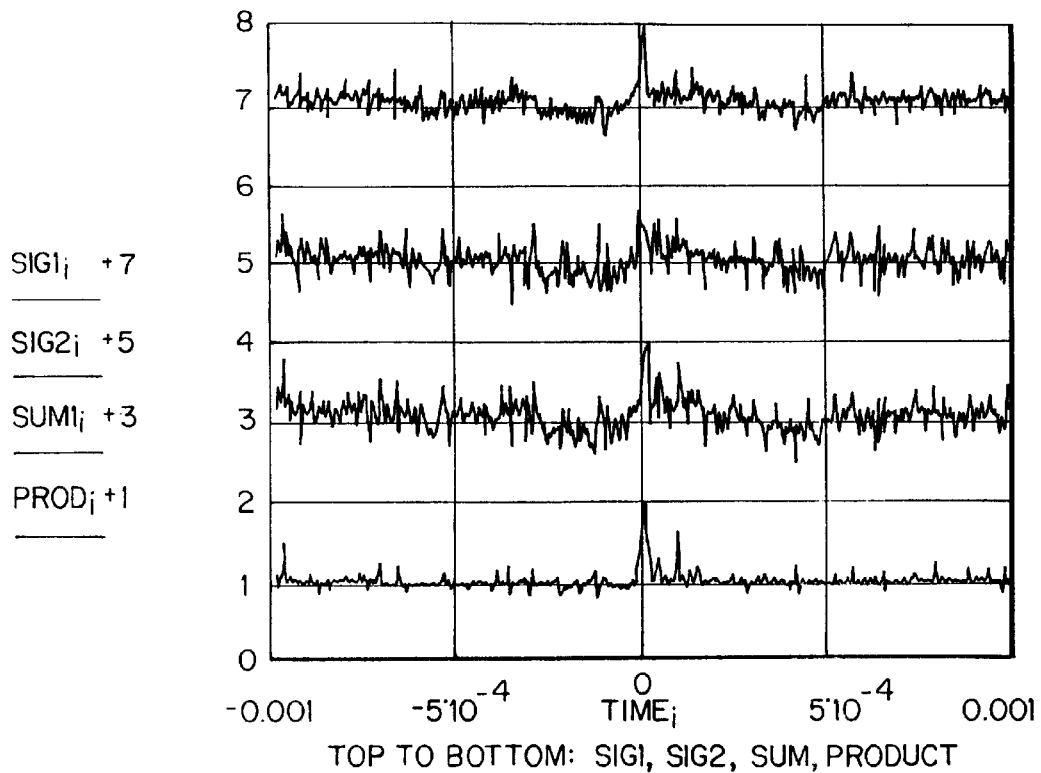
Fig_7
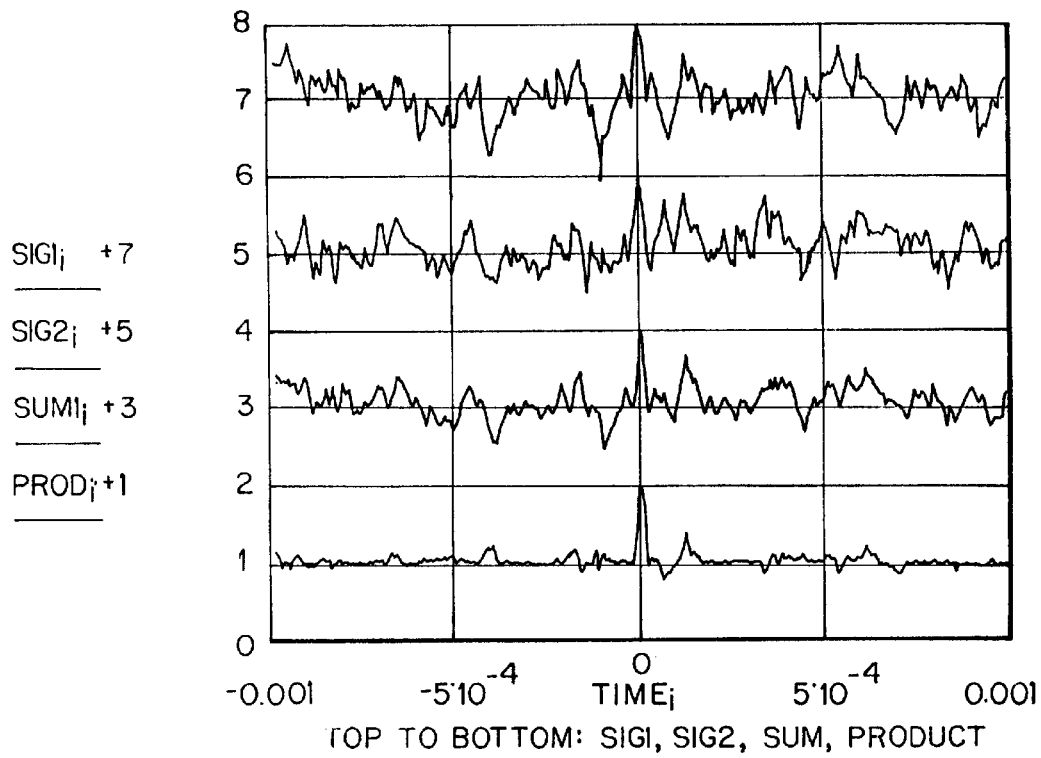
Fig_8

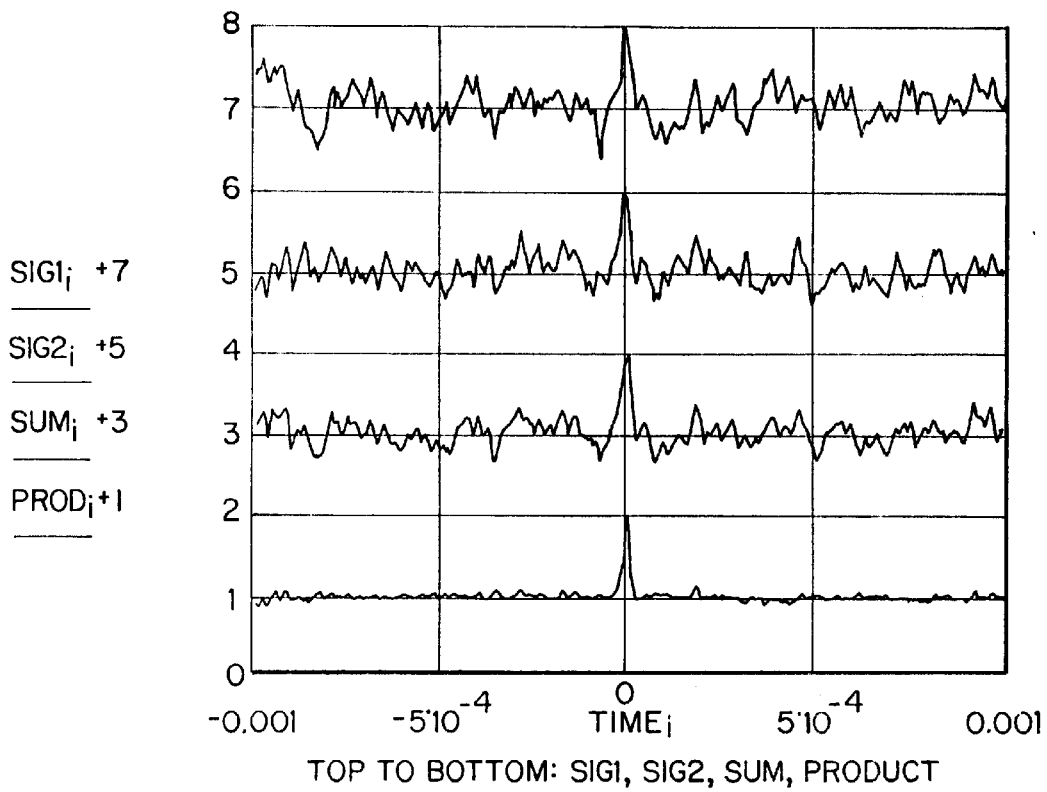
Fig_9
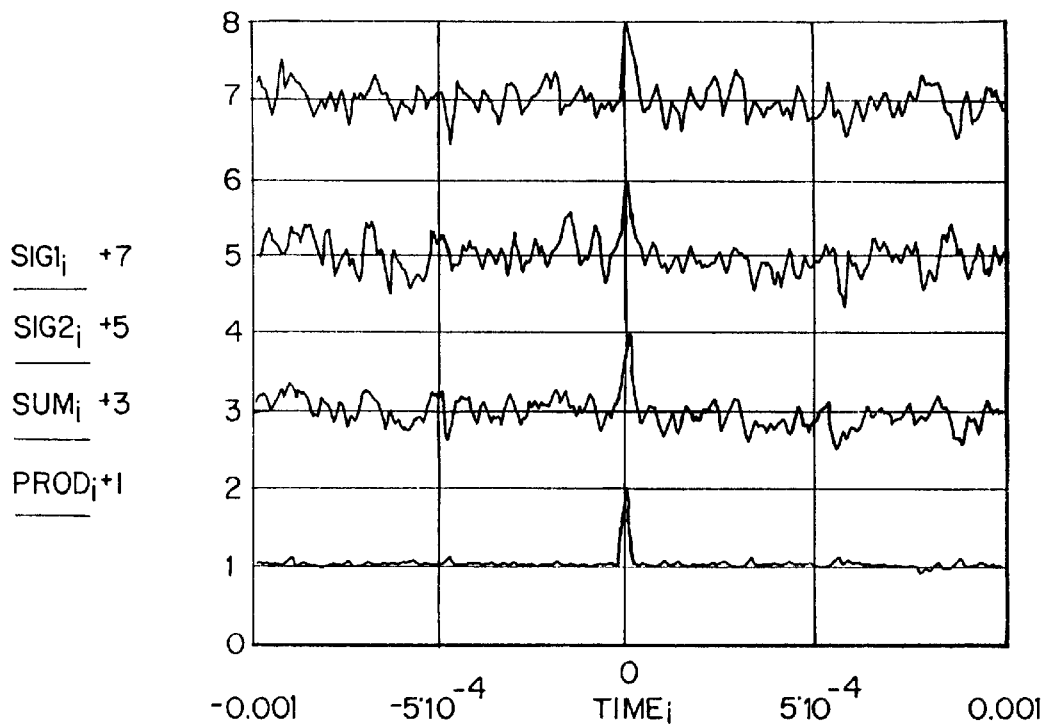
Fig_10

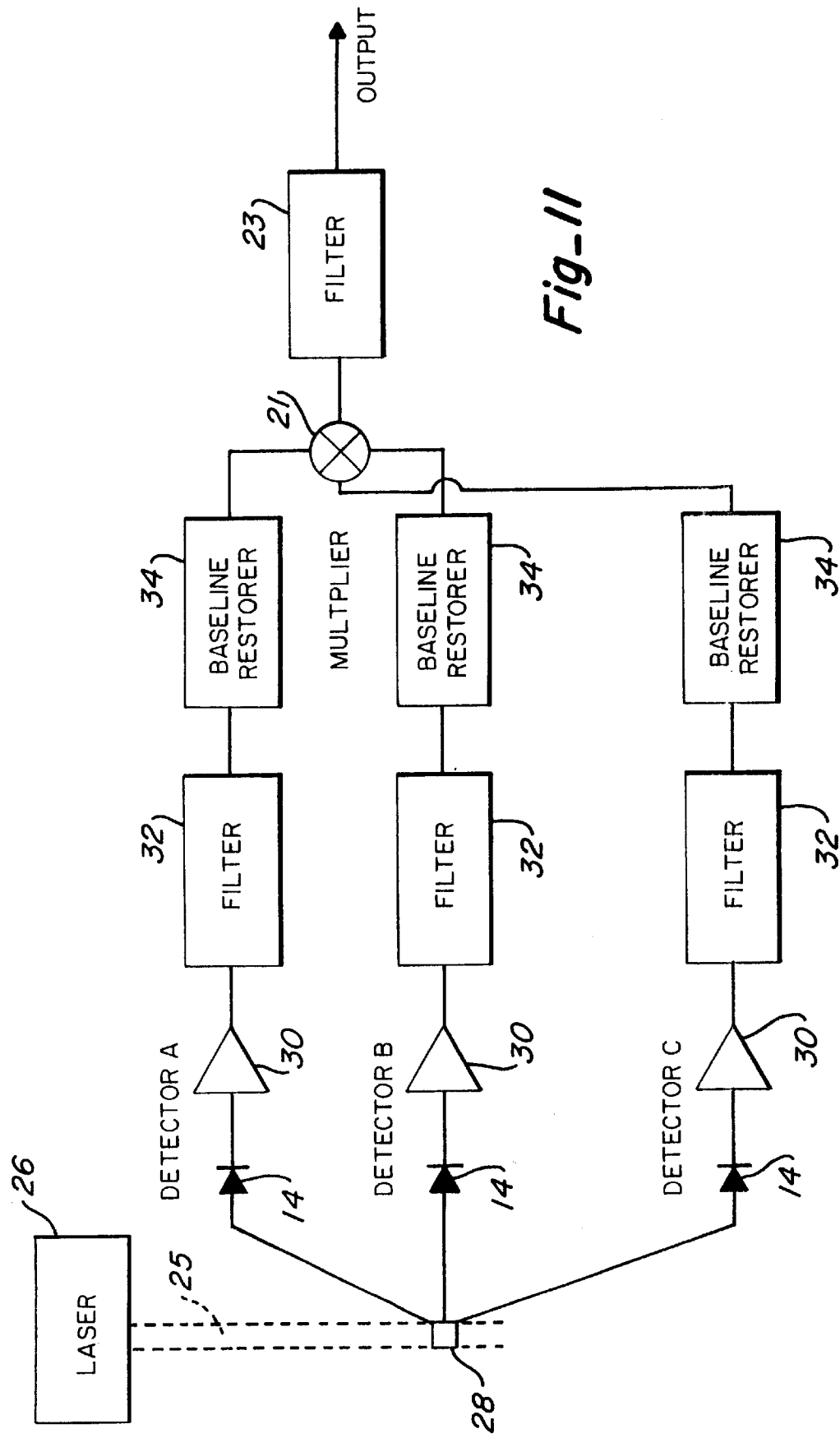
Fig_11

NOISE REDUCTION UTILIZING SIGNAL MULTIPLICATION

FIELD OF THE INVENTION

This invention relates to electrical signal noise reduction, and, more particularly, relates to noise reduction utilizing signal multiplication to enhance detection of signals indicative of the same event, such as light scattered by particles at a viewing area in a particle measuring device.

BACKGROUND OF THE INVENTION

It is well known that electrical signals indicative of information can be formed, or generated, and then conveyed, with the information being thereafter extracted from the signals for utilization. Such is the case, for example, where electrical signals are formed with pulses therein indicative of light scattered by particles at a sensing, or viewing, area and then coupled to a detector where the electrical signals are processed to indicate a parameter, such as size, of the particles (see, for example, U.S. Pat. No. 4,798,465).

Since pulses indicative of information included in a signal can be detected only where the pulse height, or magnitude, exceeds that of the noise included in the signal, with such detection being more difficult as the magnitude of the noise approaches that of the information-carrying pulses, various systems have heretofore been suggested, and/or utilized, that provide for reduction of noise relative to the magnitude of the information-carrying pulses in the signal (i.e., have improved the signal-to-noise ratio), and such systems have included techniques used in conjunction with reduction of noise in signals having pulses therein indicative of light scattered by particles, with such techniques including signal subtraction (see, of example, U.S. Pat. Nos. 4,893,928 and 5,467,189) and summing of signals (see, for example, U.S. Pat. Nos. 4,917,496 and 5,153,926).

SUMMARY OF THE INVENTION

This invention provides improved noise reduction utilizing signal multiplication, and is particularly useful for effecting noise reduction in a signal indicative of light scattered by particles to enable enhanced identification of a parameter of the particles, such as size.

Noise reduction is effected by multiplying together electrical signals from a plurality of channels each of which signals includes noise and pulses indicative of the same event, such as light scattered by the particles at a sensing, or viewing, area that is commonly sensed, or viewed, by a separate detector in each of the plurality of channels.

The output from each channel is preferably amplified, passed through matched low-pass filters to enhance pulse detection, and then passed through a baseline restorer to remove DC components from the noise present in the signal, prior to coupling of the signals to a multiplier.

At the multiplier, the peak values of the pulses included in the signal from each of the channels multiply, as do the variances of uncorrelated noise included in the signal from each of the channels, resulting in multiplication of the signal-to-noise ratio, and hence improvement in signal-to-noise.

It is therefore an object of this invention to provide improved noise reduction utilizing signal multiplication.

It is another object of this invention to provide improved noise reduction utilizing multiplication of signals indicative of light scattered by particles.

It is still another object of this invention to provide improved noise reduction effected by multiplying together electrical signals from a plurality of channels each of which signals includes noise and pulses indicative of the same, or common, event, such as light scattered by particles at a viewing area that is commonly detected, or sensed, by a separate detector in each of the plurality of channels.

It is still another object of this invention to provide improved noise reduction effected by multiplying together electrical signals from a plurality of channels each of which includes amplification, filtering and DC component noise removal in each channel prior to multiplication of the signals together.

It is still another object of this invention to provide improved noise reduction effected by multiplying together electrical signals from a plurality of channels after the signals in each channel have been processed to remove DC components of noise in the signals so that multiplication of the resulting signals causes information-carrying pulses to be multiplied along with variances of uncorrelated noise to thereby provide improvement in signal-to-noise.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 1 is a block diagram illustrating the invention;

FIG. 2 is a block diagram illustrating a digital implementation of the multiplier shown in FIG. 1;

FIGS. 3 through 10 illustrate waveforms using this invention as shown in FIG. 1; and FIG. 11 is a block diagram illustrating the invention with a plurality greater than two of input channels to the multiplier.

DESCRIPTION OF THE INVENTION

A fundamental challenge in a detection system utilizing light scattering is to distinguish the information-carrying pulses from noise in the signal. In this invention, an improved signal-to-noise (S/N) ratio is achieved by enhancement of information-carrying pulses in the signal relative to the variance of the noise in the signal.

Signal providers, specifically indicated as detectors 14 in channels 16 and 17 in FIG. 1, are utilized to separately sense, or detect, the same event and responsive thereto, provide separate outputs that include pulses indicative of the event embedded in noise.

The electrical signals formed, or generated, by each detector 14 is processed in a signal processor 19 in each of channels 16 and 17 and the outputs from each signal processor is coupled to multiplier 21 where the outputs are multiplied together (i.e., multiplied by one another) and the output is then coupled from the multiplier, preferably through filter 23, to provide an output having enhanced signal-to-noise ratio.

Noise reduction according to this invention is particularly well suited for use in connection with a particle detecting device having light 25, such as laser light, from a light source 26, such as a laser directed into a viewing, or sampling, area 28, as indicated in FIG. 1, so that particles at the viewing area scatter light that is then detected by light sensitive detectors to provide electrical output signals that include pulses indicative of detected scattered light.

As also indicated in FIG. 1, detectors 14 sense, or detect, events occurring at the same viewing area (or sense, or detect events occurring at the same portion of an overall viewing area), so that the output signals generated, or provided, by the detectors in channels 16 and 17 include information-carrying pulses indicative of the events, such as scattered light, occurring in the viewing area.

The output signals from the detectors, after processing in accordance with this invention to enhance the pulses relative to the then present noise, are further processed to provide information indicative of a parameter of the particle, such as particle size, with such further processing being, for example, as shown in U.S. Pat. No. 4,798,465, hereby incorporated herein by reference.

Channels 16 and 17 are identical, and, as indicated in FIG. 1, each channel includes amplification stage 30 (including one or more amplifiers, as needed, to convert the input signals to useable levels), filter stage 32 (including matched low-pass filters that provide nearly optimum detection of pulses in random noise), and a baseline restorer stage 34 (including a noise component adjuster to remove any DC components from the noise, while substantially ignoring the pulses).

Multiplication of the processed signals at multiplier 21 can be effected by use of analog multiplication (as indicated in FIG. 1), or, alternately, could be effected by use of digital multiplication, using analog-to-digital (A/D) converters 36 and a digital multiplier 37, as indicated in FIG. 2.

The signals before multiplication are composed of pulses that are approximately Gaussian in shape and are embedded in random noise. The noise is generated by shot noise in the illumination source, shot noise in the detector, thermal noise in the processing electronics, and molecular scattering noise (and can be accurately modeled as being normally distributed random noise).

It is important that the signals be processed so that the noise has, as near as possible, zero mean value, which is ensured in this invention through use of baseline restorer stage 34 in each channel.

One way to define the signal-to-noise ratio for the system of this invention is as the ratio of the peak of a particle pulse to the variance of the noise. Obviously, the result of multiplying the pulses is that the peak of the product signal is just the product of the peaks of the two multiplier signals. It can be shown that the variance of the products of two uncorrelated random signals is:

$$\sigma_{xy}^2 = \sigma_x^2 \sigma_y^2 + \mu_x^2 \sigma_y^2 + \mu_y^2 \sigma_x^2$$

where $\sigma_{xy}$ is the standard deviation of the product, $\sigma_x$ is the standard deviation of signal x, $\sigma_y$ is the standard deviation of signal y, $\mu_x$ is the mean value of signal x, and $\mu_y$ is the mean value of signal y.

If the random signals have zero mean values, the last two terms in the above equation vanish. The result is that the variance of the product of two random, uncorrelated, zero mean signal is the product of their variances.

Since the variances of the noise terms multiply when the signals are multiplied together, and the peek values of the pulses also multiply, it is clear that the signal-to-noise ratios also multiply. This shows that if the unmultiplied signals have signal-to-noise ratios that are greater than one, the result of multiplying the signals is a signal with improved signal-to-noise.

Utilizing this invention, scope data for eight groups, as shown in FIGS. 3 through 10, was processed using the following for each group:

data1=READPRN multna$_{tab}$, with na being 1a through 8a for the eight groups data2=READPRN mult1b$_{tab}$, with na being 1a through 8a for the eight groups $prod = \overline{(sig1 \times sig2)}$ $sum = sig1 + sig2$ $i = 0 \ldots rows(sig1) - 1$ $sig1 = submatrix(data, 0, rows(data1) - 1, 1, 1)$ $sig2 = submatrix(data2, 0, rows(data1) - 1, 1, 1)$ $time = submatrix(data1, 0, rows(data1) - 1, 0, 0)$ The signals were then normalized so that the peak values were unity:

$m = max(sig1) \quad sig1_i = sig1_i/m$
$m = max(sig2) \quad sig2_i = sig2_i/m$
$m = max(prod) \quad prod_i = prod_i/m$
$m = max(sum) \quad sum_i = sum_i/m$ The standard deviations of the noise sequence (using the first 400 samples) were then calculated, with the following results:

$sig1_{stdev} = stdev(submatrix(sig1,0,399,0,0))$, $sig2_{stdev} = stdev(submatrix(sig2,0,399,0,0))$, $sum_{stdev} = stdev(submatrix(sum,0,399,0,0))$, and $prod_{stdev} = stdev(submatrix(prod,0,399,0,0))$—common to all eight groups $sig1_{stdev} = 0.108$ (Group 1); 0.161 (Group 2); 0.126(Group 3); 0.126 (group 4); 0.113 (Group 5); 0 249 (Group 6); 0.22 (Group 7); and 0.166 (Group 8)

$sig2_{stdev} = 0.121$ (Group 1); 0.126 (Group 2); 0.179 (Group 3); 0.193 (Group 4); 0.147 Group 5); 0.195 (Group 6); 0.156 (Group 7); and 0.187 (Group 8)

$sum_{stdev} = 0.101$ (Group 1); 0.1 (Group 2); 0.135 (Group 3); 0.143 (Group 4); 0.156 (Group 5); 0.184 (Group 6); 0.147 (Group 7); and 0.141 (Group 8)

$prod_{stdev} = 0.019$ (Group 1); 0.024 (Group 2); 0.042 (Group 3); 0.046 (Group 4); 0.047 (Group 5); 0.046 (Group 6); 0.034 (Group 7); and 0.025 (Group 8)

The signal-to-noise ratio was then calculated assuming that the amplitude of the pulse was 1, with the following results:

$sig1_{sn} = 1/sig1_{stdev} = 9.277$ (Group 1); 6.228 (Group 2); 7.917 (Group 3); 7.925 (Group 4); 8.876 (Group 5); 4.015 (Group 6); 4.551 (Group 7); and 6.01 (Group 8)

$sig2_{sn} = 1/sig2_{stdev} = 8.224$ (Group 1); 7.936 (Group 2); 5.576 (Group 3); 5.18 (Group 4); 6.782 (Group 5); 5.128(Group 6); 6.42 (Group 7); and 5.345 (Group 8)

signal 1 and signal 2 $sum = sum_{sn} = 1/sum_{stdev} = 9.921$ (Group 1); 10.042 (Group 2); 7.387 (Group 3); 7.006 (Group 4); 6.417 (Group 5); 5.423 (Group 6); 6.781 (Group 7); and 7.097 (Group 8)

signal 1 times signal 2 = $prod_{sn} = 1/prod_{stdev} = 52.046$ (Group 1); 42.143 (Group 2); 23.589 (Group 3); 21.539 (Group 4); 21.256 (Group 5); 21.579 (Group 6); 29.463 (Group 7); and 40.516 (Group 8)

improvement ratio = $prod_{sn}/sum_{sn} = 5.246$ (Group 1); 4.197 (Group 2); 3.193 (Group 3); 3.074 (Group 4); 3.312 (Group 5); 3.979 (Group 6); 4.345 (Group 7); and 5.709 (Group 8).

This invention can be extended to systems that have more than two input signals by multiplying the signals from all inputs together (such as, for example, by multiplying three signal inputs together at multiplier 13, as indicated in FIG. 11). This results in a product signal that has a signal-to-noise ratio that is the product of the individual signals.

As can be appreciated from the foregoing, this invention provides an improved system and method for achieving noise reduction through use of signal multiplication.

What is claimed is:

1. A noise reduction system providing enhanced signal-to-noise ratio, said system comprising:

first and second signal providers each providing output signals that include pulses indicative of the same event, with said pulses being embedded in noise and having a magnitude greater than the variance of said noise;

first and second signal processors connected with different ones of said first and second signal providers and providing separate processed outputs indicative of said output signals received from said first and second signal providers; and a multiplier receiving said processed outputs from said first and second signal processors and, responsive thereto, multiplying said processed outputs together to provide an output signal having an enhanced signal-to-noise ratio.

2. The system of claim 1 wherein said first and second signal providers include detectors for sensing said event and, responsive thereto, providing said pulses.

3. The system of claim 2 wherein said detectors sense light scattered by particles at a viewing area as said event.

4. The system of claim 3 wherein said system is included in a particle measuring device.

5. The system of claim 1 wherein said first and second signal processors include noise component adjusters whereby said processed outputs of said first and second processors include noise at substantially zero mean value.

6. The system of claim 5 wherein said noise component adjusters substantially remove DC noise components from said processed outputs.

7. The system of claim 1 wherein said first and second signal processors also include matched low-pass filters to augment detection of said pulses in said separate output signals.

8. The system of claim 1 wherein said multiplier is one of an analog multiplier and a digital multiplier.

9. The system of claim 1 wherein said system includes a third signal provider providing output signals that include pulses indicative of an event commonly viewed by said first, second, and third signal providers, and a third signal processor connected with said third signal provider to provide a processed output signal indicative of said output signals received from said third signal provider with said processed output signal also being coupled to said multiplier.

10. A noise reduction system providing enhanced signal-to-noise ratio, said system comprising:

first and second detectors each providing separate output signals that include pulses indicative of the same event with said pulses being embedded in noise and having a magnitude greater than the variance of said noise;

first and second signal processors connected with different ones of first and second detectors, each of said processors including signal adjusters for substantially removing DC noise components in said output signals received from said detectors, and thereafter providing separate processed outputs indicative of said output signals received from said first and second detectors; and a multiplier receiving said processed outputs from said first and second signal processors and, responsive thereto, multiplying said processed outputs by one another to provide an output signal having enhanced signal-to-noise ratio.

11. The system of claim 10 wherein said system is a part of a particle detecting device, and wherein said detectors sense light scattered by particles at a viewing area as said event.

12. The system of claim 11 wherein said first and second signal processors also include amplifiers and matched low-pass filters to augment detection of said pulses in said separate output signals.

13. A noise reduction system providing enhanced signal-to-noise ratio, said system comprising:

first and second detectors each providing separate output signals that include pulses indicative of light scattered at a sampling area commonly viewed by said detectors with said pulses being embedded in noise and having a magnitude greater than the variance of said noise;

first and second signal processors connected with different ones of said first and second detectors to receive said output signals therefrom and providing separate processed outputs having noise at substantially zero mean value; and a multiplier receiving said processed outputs from said first and second signal processors and, responsive thereto, multiplying said processed outputs by one another to provide an output signal having enhanced signal-to-noise ratio.

14. The system of claim 13 wherein said system is part of a particle measuring device.

15. The system of claim 13 wherein said first and second signal processors include amplifiers and matched low-pass filters to augment detection of said pulses in said separate output signals.

16. The system of claim 13 wherein said system includes a third detector providing output signals that include pulses indicative of an event commonly received by said first, second, and third detectors, and a third signal processor connected with said third detector to provide a processed output signal indicative of output signals received by said with said processed output signal also being coupled to said multiplier.

17. A method for noise reduction providing enhanced signal-to-noise ratio, said method comprising:

separately sensing an event and separately providing output signals that include pulses indicative of said event with said pulses being embedded in noise and having a magnitude greater than the variance of said noise;

processing said output signal and separately providing outputs with noise at substantially zero mean value; and multiplying said processed outputs by one another to provide an output signal having enhanced signal-to-noise ratio.

18. The method of claim 17 wherein said step of sensing an event includes sensing of light scattered by particles at a viewing area as said sensed event.

19. The method of claim 17 wherein said method also includes augmenting said pulses.

20. The method of claim 17 wherein said step of separately sensing an event includes thrice separately sensing said event and providing separate output signals that are separately processed so that each processed output has noise at said substantially zero mean value, and wherein said step of multiplying said processed outputs by one another is effected by multiplying said three processed outputs by one another to provide said output signal having enhanced signal-to-noise ratio.

* * * * *